United States Patent
Ormeci et al.

(10) Patent No.: US 10,768,117 B2
(45) Date of Patent: Sep. 8, 2020

(54) DEVICE FOR DETECTING ALGAE CONCENTRATION USING FIRST DERIVATIVE OF VISIBLE LIGHT ABSORBANCE

(71) Applicant: REAL TECH INC., Whitby (CA)

(72) Inventors: Banu Ormeci, Manotick (CA); Andrew Glover, Oshawa (CA); Kerim Kollu, Oshawa (CA)

(73) Assignee: REAL TECH HOLDINGS INC., Whitby (CA)

( * ) Notice: Subject to any disclaimer, the term of this patent is extended or adjusted under 35 U.S.C. 154(b) by 99 days.

(21) Appl. No.: 16/304,452

(22) PCT Filed: May 24, 2017

(86) PCT No.: PCT/CA2017/050629
§ 371 (c)(1),
(2) Date: Nov. 26, 2018

(87) PCT Pub. No.: WO2017/201622
PCT Pub. Date: Nov. 30, 2017

(65) Prior Publication Data
US 2019/0145901 A1    May 16, 2019

Related U.S. Application Data

(60) Provisional application No. 62/340,956, filed on May 24, 2016.

(51) Int. Cl.
*G01N 21/85*    (2006.01)
*G01N 21/31*    (2006.01)
(Continued)

(52) U.S. Cl.
CPC .............. *G01N 21/85* (2013.01); *C12Q 1/06* (2013.01); *G01J 3/12* (2013.01); *G01J 3/42* (2013.01);
(Continued)

(58) Field of Classification Search
CPC .... G01N 21/85; G01N 21/31; G01N 33/1893; G01N 2021/8466; G01N 2201/12; C12Q 1/06; G01J 3/12; G01J 3/42
See application file for complete search history.

(56) References Cited

U.S. PATENT DOCUMENTS

| | | | |
|---|---|---|---|
| 7,027,149 B2 | 4/2006 | O'Mongain | |
| 2004/0233447 A1 | 11/2004 | White et al. | |
| 2006/0132762 A1* | 6/2006 | Kirkpatrick | G01J 3/433 356/300 |

FOREIGN PATENT DOCUMENTS

| | | |
|---|---|---|
| EP | 0915338 A2 | 5/1999 |
| EP | 0915338 A3 | 3/2000 |
| WO | 2014156363 A1 | 10/2014 |

OTHER PUBLICATIONS

Demetriades-Shah, T.H., Steven, M.D. and Clark, J.A. (1990) High resolution derivative spectra in remote sensing. Remote Sensing of Environment 33, pp. 55-64.
(Continued)

*Primary Examiner* — Jamil Ahmed
(74) *Attorney, Agent, or Firm* — Hill & Schumacher

(57) ABSTRACT

Monitoring and detection of algae in surface water and wastewater is of significant importance, yet there is currently no quick and simple method to achieve this. The present work illustrates a new method to determine the concentration of algae in water and wastewater samples using spectrophotometry, the first derivative of absorbance, and a smoothing technique applied to the first derivative of absorbance (e.g. Savitzky-Golay). The relationship between algal
(Continued)

concentration and absorbance for three types of water samples (distilled, surface, and wastewater) was determined in the visible wavelength range, and the effect of using the first derivative of absorbance method on improving algal concentration detection limit was established. Using the first derivative of absorbance method improves algal detection limits, reduces the effect of background absorbance and the resolution of overlapping spectra. The presence of algae in water can cause a number of problems, and the method presented here can be used to effectively monitor algal concentration in various types of water samples and provide necessary information for decision making purposes.

11 Claims, 3 Drawing Sheets

(51) Int. Cl.
  *G01J 3/42* (2006.01)
  *G01J 3/12* (2006.01)
  *G01N 33/18* (2006.01)
  *C12Q 1/06* (2006.01)
  *G01N 21/84* (2006.01)

(52) U.S. Cl.
  CPC ......... *G01N 21/31* (2013.01); *G01N 33/1893* (2013.01); *G01N 2021/8466* (2013.01); *G01N 2201/12* (2013.01)

(56) References Cited

OTHER PUBLICATIONS

Gaigalas, A. K. Hua-Jun He and Wang, L. (2009) Measurement of Absorption and Scattering with an Integrating Sphere Detector: Application to Microalgae. Journal of Research of the National Institute of Standards and Technology 114(2), pp. 69-81.

Liang, H., Nan, J., Zhang, X., Chen, Z., Tian, J. and Li, G. (2010) A novel on-line optical method for algae measurement. Journal of Chemical Technology and Biotechnology 85(10).

Rodrigues, L.H.R., Arenzon, A., Raya-Rodriguez, M.T. and Fontoura, N.F. (2011) Algal density assessed by spectrophotometry: A calibration curve for the unicellular algae Pseudo kirch neriella subcapitata. Journal of Environmental Chemistry and Ecotoxicology 3(8), pp. 225-228.

Erk, N. (2000). Quantitative analysis of chlorpheniramine maleate and phenylephrine hydrochloride in nasal drops by differential-derivative spectrophotometric, zero-crossing first derivative UV spectrophotometric and absorbance ratio methods. Journal of Pharmaceutical and Biomedical Analysis, 23(6), pp. 1023-1031.

Richardson, T. I., Lawrenz, E., Pinckney, J. L., Guajardo, R. C., Walker, E. A., Paerl, H. W., & MacIntyre, H. L. (2010). Spectral fluorometric characterization of phytoplankton community composition using the Algae Online Analyser. Water Research, 44(8), pp. 2461-2472.

Rundquist, D. C., Han, L., Schalles, J. F., & Peake, J. S. (1996). Remote measurement of algal chlorophyll in surface waters: the case for the first derivative of reflectance near 690 nm. Photogrammetric Engineering & Remote Sensing, 62(2), pp. 195-200.

Wiggins, K., Palmer, R., Hutchinson, W., & Drummond, P. (2007). An investigation into the use of calculating the first derivative of absorbance spectra as a tool for forensic fibre analysis. Science & Justice, 47(1), pp. 9-18.

Zamyadi, A., Choo, F., Newcombe, G., Stuetz, R., & Henderson, R. K. (2016). A review of monitoring technologies for realtime management of cyanobacteria: recent advances and future direction. Trends in Analytical Chemistry, 82, pp. 1-14.

Rundquist et al. "Remote Measurement of Algal Chlorophyll in Surface Waters: The Case for the First Derivative of Reflectance Near 690 nm." Photogrammetric Engineering & Remote Sensing. vol. 62, No. 2, Feb. 1996 (Feb. 1996), pp. 195-200.

Sanchez et al. "Derivative Ultraviolet-Visible Region Absorption spectrophotometry and its analytical applications." Talanta, vol. 35, No. 10, pp. 753-761 (1988).

International Search Report for international application No. PCT/CA2017/050629, dated Sep. 19, 2017.

\* cited by examiner

DEVICE FOR DETECTING ALGAE CONCENTRATION USING FIRST DERIVATIVE OF VISIBLE LIGHT ABSORBANCE

FIELD

The invention relates to the field of visible light spectrophotometry and more particularly it relates to a device for detecting algae concentration using first derivative of visible light absorbance.

BACKGROUND

The presence of algae in both surface and wastewater is one of the main causes of water quality deterioration (Al-Zboon and Al-Suhaili, 2009; Rodrigues et al., 2011). Algal growth in different parts of conventional wastewater treatment plants or aerated lagoon systems can result in false indications in the final effluent parameters, such as TSS, $CBOD_5$ and COD (Heng et al., 2010; Chow et al., 1999; Gitzgerald, 1964). In surface water, the presence of algae creates nuisance surface scum, poor water clarity, and noxious odours (Abdel-Raouf et al., 2012; Aly and Sami, 2014). If this surface water is used to produce drinking water, the algae may lead to problems in the drinking water treatment process, such as reduced filter runs and an increase in the amount of disinfectant needed, which can increase the cost of the treatment (Horan, 1990).

In order to set up an efficient control and treatment process to minimize algal concentration in water samples, it is necessary to have access to a concentration measurement method which is quick, simple, and accurate, and which can detect low algal concentrations in different types of water. The methods currently used to determine algal concentration in different water samples include algal number, as prescribed in the Standard Methods for the Examination of Water and Wastewater (APHA, 1985), and the determination of chlorophyll extract concentration in relation to total algal concentration (Wasmund et al., 2006; Jones and Lee, 1982). Both of these methods are labour and time intensive, expensive, and require extensive laboratory preparation. Moreover, it is not clear how efficient the chlorophyll extraction process is or how its results are related to the real algal concentration in water solutions.

Recently, the use of real-time and inline spectrophotometric methods at water and wastewater treatment plants to measure different parameters, such as total organic carbon, disinfection by-product precursors, nitrates, and UV transmittance for UV disinfection have increased dramatically (James et al., 2003; Langergraber et al., 2004; Gibbons and Örmeci, 2013; Al Momani and Ormeci, 2014). These measurements are considered practical, quick, simple, and accurate for these industries.

Different studies have reported that the absorbance measurements of algae in water produce a spectrum with a maximum absorbance near the wavelength of red light (540-690 nm) (Gaigalas et al., 2009; UGWU et al., 2007; Liang et al., 2009; Sung et al., 2010). In some types of water and wastewater, the accuracy of the spectrophotometric measurements is affected by water turbidity and by the presence of other constituents in the water sample that mask the absorbance response or produce high levels of noise in the spectral background.

Spectral first and higher-order derivatives have been used by different studies to facilitate the location of the critical wavelength, to reduce low-frequency background noise, and to resolve overlapping spectra (Demetriades-Shah et al., 1990). However, it appears that no research work has explored the use of the first derivative of the absorbance spectra to determine the concentration of algae in an aqueous solution.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a system for detecting algae, comprising: an online spectrophotometer configured to measure an absorbance level of a sample from a monitored source, and a processor that is configured to apply an algorithm to the measured absorption level to determine the concentration of algae in the monitored source, wherein the detection algorithm is derived by calculating the first derivative of absorbance values for the monitored source and applying a calibration set of the first derivative of absorbance values obtained from a controlled source with known concentrations of algae.

In addition to the exemplary aspects and embodiments described above, further aspects and embodiments will become apparent by reference to the figures and by study of the following detailed description.

Thus the present disclosure provides a device for detecting algae in water, comprising:
  (i) a light source to generate light beams of electromagnetic radiation in the visible light spectrum;
  (ii) a flow cell containing a water sample including windows to allow said light beams to transmit through said flow cell and water sample;
  (iii) a spectrometer unit that receives said transmitted light beam penetrating said sample in said flow cell, and resolves said incident light beam into a specific visible absorbance spectrum pertaining to said sample; and
  (iv) a processor connected to said spectrometer unit programmed to
    a. compute the derivative of the measured visible absorbance spectrum through said flow cell;
    b. compute from the derivative spectra the concentration of varying types of algae.

The device is configured to detect the concentration of various algae species.

The device may be operated to measure the concentration of algae in distilled water, surface water, or wastewater.

The processor may be programmed to apply a smoothing technique to improve the signal to noise ratio in the absorbance data. An exemplary non-limiting smoothing technique is the Savitzky-Golay smoothing technique.

The device is constructed so that samples can be directly placed into the spectrometer unit for analysis with no additional sample preparation requirements.

The light source may be a tungsten lamp.

Alternatively, the light source may be an LED based light source.

The spectrometer unit may be a photodiode array based spectrometer.

Alternatively, the spectrometer unit is a monochromator.

The device may be configured to be immersed in a sample water such that the sample water is free to flow in and out of a substantially open flow cell area.

The flow cell is configured to allow sample water to flow through either continuously or in successive batches from a sample source to a sample drain.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
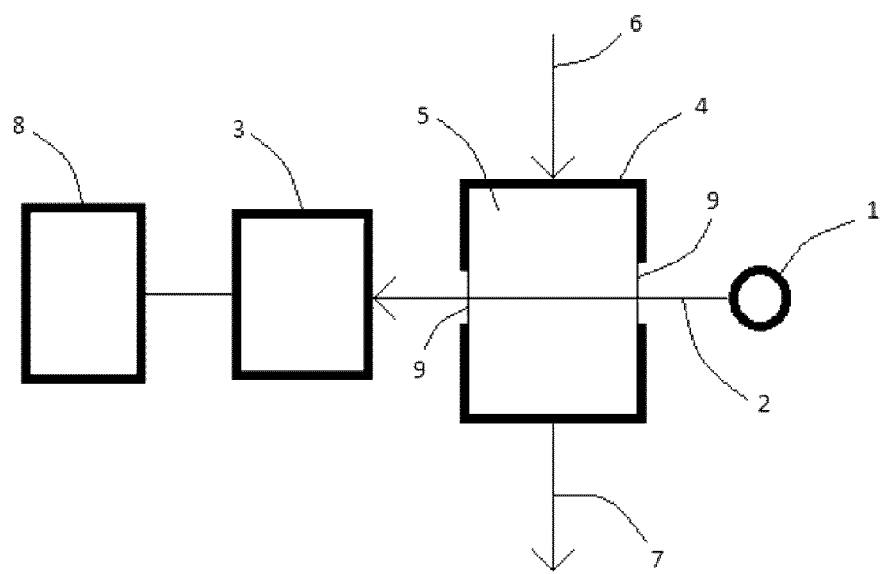
FIG. 1 shows the preferred embodiment of the invention, and describes its apparatus.
Figure 2:
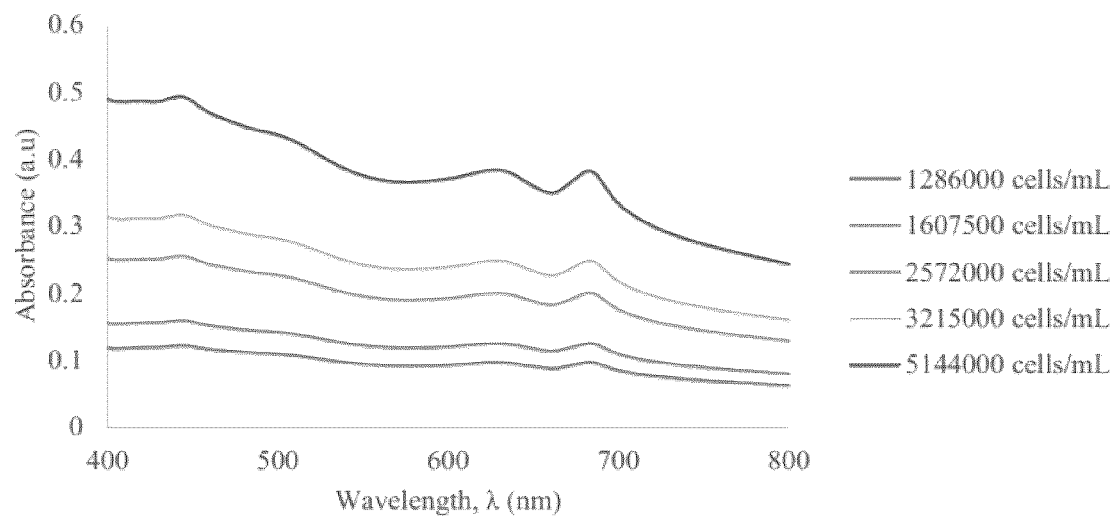
FIG. 2 shows the absorbance scans of various concentrations of *Microcystis aeruginosa* CPCC 299 in deionized water.
Figure 3:
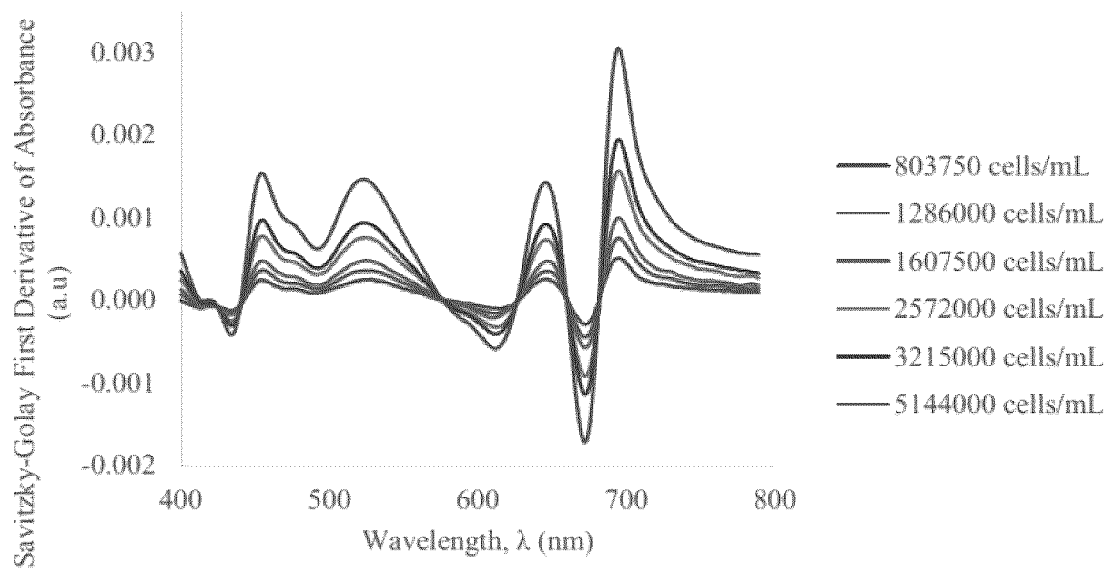
FIG. 3 shows the Savitzky-Golay first derivative of the absorbance scans of various concentrations of *Microcystis aeruginosa* CPCC 299 in deionized water.

Various embodiments and aspects of the disclosure will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

An embodiment of the invention includes the apparatus described by FIG. 1. A light source (1) provides light of the required wavelengths for detection of the various algae species to be detected in water, generally in the red light region of the visible spectrum. In the preferred embodiment the light source (1) is a broadband light source in the visible light spectrum, where the broadband light source could be a tungsten lamp, or an LED based light source. A light beam (2) from the light source transmits through a flow cell (4) containing the water sample under test (5) to a spectrometer unit (3). The flow cell allows sample water to flow through either continuously or in successive batches. In the preferred embodiment the sample water flows from a sample source (6) to a sample drain (7) continuously. The flow cell (4) contains windows (9) to allow the light to transmit through the flow cell. Note that in another embodiment the system could be immersed in a sample fluid such that the sample water is free to flow in and out of a substantially open flow cell area. The spectrometer unit (3) resolves the incident light into a specific absorbance spectrum of the water sample under test (5) as shown in FIG. 2. A computer system (8) connected to the spectrometer unit (3) has been programmed specifically to compute the first derivative of the measured absorbance spectrum through the flow cell, apply a smoothing technique to the first derivative (such as, but not limited to, the Savitzky-Golay technique as shown in FIG. 3), and to compute the concentration of various types of algae from the first derivative of absorbance spectra.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

Abdel-Raouf, N., Al-Homaidan, A. A. and Ibraheem, I. B. M. (2012) Microalgae and wastewater treatment. Saudi Journal of Biological Sciences 19(3), 257-275.

Al Momani, F. A. and Örmeci, B. (2014) Measurement of polyacrylamide polymers in water and wastewater using an in-line UV-vis spectrophotometer. Journal of Environmental Chemical Engineering 2(2), 765-772.

Aly, O. H. I. and Sami, A. I. D. (2014) The Control of Algae in the Effluent of Oxidation Ponds. International Journal of Engineering Research & Technology 3 (1).

Al-Zboon, K. and Al-Suhaili, R. (2009) Improvement of Water Quality in a Highly Polluted River in Jordan. Jordan Journal of Civil Engineering, 3 (3).

APHA, A., WPCF (1985) Standard methods for the examination of water and wastewater, American Public Health Association.

Ugwu, C. U., Aoyagi, H. and Uchiyama, H. (2007) Influence of irradiance, dissolved oxygen concentration, and temperature on the growth of *Chlorella sorokiniana*. Photosynthetica 45 (2), 309-311.

Chow C. W. K, Drikas M, House J, Burch M D and RMA, V. (1999) The impact of conventional water treatment processes on cells of the cyanobacterium *Microcystis aeruginos*. Water Res 33, 3253-3262.

Demetriades-Shah, T. H., Steven, M. D. and Clarke, J. A. (1990) High resolution derivative spectra in remote sensing. Remote Sensing of Environment 33, 55-64.

Langergraber, G., Fleischmann, N., Hofstaedter, F., Weingartner, A., Lettl, W. (2004) Detection of (unusual) changes in wastewater composition using UV/VIS spectroscopy. Water Intelligence Online, IWA Publishing.

Gaigalas, A. K. Hua-Jun He and Wang, L. (2009) Measurement of Absorption and Scattering with an Integrating Sphere Detector: Application to Microalgae. Journal of Research of the National Institute of Standards and Technology 114(2), 69-81.

Gibbons, M. K. and Örmeci, B. (2013) Quantification of polymer concentration in water using UV-Vis spectroscopy. Journal of Water Supply: Research and Technology 62 (4), 205-213.

Gitzgerald, G. P. (1964) The Effect of Algae on BOD Measurements. J Water Pollution Control Fed 36(12), 1524-1542.

Heng, L., Jun, N., Xinxin, Z., Zhonglin, C., Jiayu T. and Guibai L. (2010) A novel on-line optical method for algae measurement. Journal of Chemical Technology and Biotechnology 85(10).

Horan, N. J. (1990) Biological Wastewater Treatment Systems. Theory and operation. John Wiley and Sons Ltd. Baffins Lane, Chickester. West Sussex PO 191 UD, England.

James, L. W., George, R. A., Brian, A. B., Miranda, S. F., Roger, F. and Kenneth, M. (2003) Evaluation of Specific Ultraviolet Absorbance as an Indicator of the Chemical Composition and Reactivity of Dissolved Organic Carbon. Environ. Sci. Technol. 37, 4702-4708.

Jones, R. A. and Lee, G. F. (1982) Chlorophyll—a raw water quality. Reserach and Technology 490.

Liang, W., Min, M., Yecong Li, Paul C., Yifeng C., Yuhuan L., Yingkuan W. and Roger R. (2009) Cultivation of Green Algae *Chlorella* sp. in Different Wastewaters from Municipal Wastewater Treatment Plant. Appl Biochem Biotechnol.

Rodrigues, L. H. R., Arenzon, A., Raya-Rodriguez, M. T. and Fontoura, N. F. (2011) Algal density assessed by spectrophotometry: A calibration curve for the unicellular algae Pseudo kirch neriella sub-capitata. Journal of Environmental Chemistry and Ecotoxicology 3(8), 225-228.

Sung Ho Oh, Min Chul Kwon, Woon Yong Choi, Yong Chang Seo, Ga Bin Kim, Do Hyung Kang, Shin Young Lee and Lee, H. Y. (2010) Long-term outdoor cultivation by perfusing spent medium for biodiesel production from *Chlorella minutissima*. Journal of Bioscience and Bioengineering 110 (2), 194-200.

Wasmund, N., Topp, I. and Schories, D. (2006) Optimising the storage and extraction of chlorophyll samples. Oceanologia, 48(1), 125-144.

What is claimed is:

1. A device for detecting algae in water, comprising:
   (i) a light source to generate light beams of electromagnetic radiation in the visible light spectrum;
   (ii) a flow cell containing a water sample including windows to allow said light beams to transmit through said flow cell and water sample;
   (iii) a spectrometer unit that receives said transmitted light beams penetrating said sample in said flow cell, and resolves said incident light beams into a specific visible absorbance spectrum pertaining to said sample;
   (iv) a processor connected to said spectrometer unit programmed to:
      a. compute the derivative of the visible absorbance spectrum through said flow cell;
      b. compute from the derivative spectra the concentration of varying types of algae.

2. A device for detecting algae according to claim 1 wherein said device can be operated to measure the concentration of algae in distilled water, surface water, or wastewater.

3. A device for detecting algae according to claim 1 wherein said processor is programmed to apply a smoothing technique to improve the signal to noise ratio in the visible absorbance spectrum.

4. A device for detecting algae according to claim 3 wherein said smoothing technique is a Savitzky-Golay smoothing technique.

5. A device for detecting algae according to claim 1 wherein samples can be directly placed into said spectrometer unit for analysis with no additional sample preparation requirements.

6. A device for detecting algae according to claim 1 wherein said light source is a tungsten lamp.

7. A device for detecting algae according to claim 1 wherein said light source is an LED based light source.

8. A device for detecting algae according to claim 1 wherein said spectrometer unit is a photodiode array based spectrometer.

9. A device for detecting algae according to claim 1 wherein said spectrometer unit is a monochromator.

10. A device for detecting algae according to claim 1 wherein said device could be immersed in a sample water such that the sample water is free to flow in and out of a substantially open flow cell area.

11. A device for detecting algae according to claim 1 wherein said flow cell allows sample water to flow through either continuously or in successive batches from a sample source to a sample drain.

* * * * *